US010247635B2

(12) United States Patent
Pickard et al.

(10) Patent No.: US 10,247,635 B2
(45) Date of Patent: Apr. 2, 2019

(54) ONLINE CHLORINE ANALYZER (71) Applicant: Hach Company, Loveland, CO (US)

(72) Inventors: Murphy Lee Pickard, Broomfield, CO (US); Peter Louis Bielawski, Fort Collins, CO (US); Russell Paul Gorham, Windsor, CO (US); Randolph Anderson, Eaton, CO (US); Rajesh Shetty, Fort Collins, CO (US); Erez Raviv, Wellington, CO (US); Timothy N. Kirk, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 0 days.

(21) Appl. No.: 15/199,726

(22) Filed: Jun. 30, 2016

(65) Prior Publication Data
US 2018/0003585 A1 Jan. 4, 2018

(51) Int. Cl.
*G01M 3/00* (2006.01)
*B01L 3/00* (2006.01)
(Continued)

(52) U.S. Cl.
CPC ............ *G01M 3/002* (2013.01); *B01L 3/502* (2013.01); *B01L 3/527* (2013.01); *G01F 1/684* (2013.01);
(Continued)

(58) Field of Classification Search
CPC ........ G01M 3/002; B01L 3/527; B01L 3/502; G01N 31/22; G01N 21/78; G01N 33/18
See application file for complete search history.

(56) References Cited

U.S. PATENT DOCUMENTS 4,925,444 A * 5/1990 Orkin ................ A61M 5/16827
 123/DIG. 13
4,938,079 A * 7/1990 Goldberg .............. G01F 1/7084
 604/65
(Continued)

FOREIGN PATENT DOCUMENTS

| JP | H0627123 | 2/1994 |
| JP | 2014001985 | 1/2014 |
| WO | 02/39071 | 5/2002 |

OTHER PUBLICATIONS

International Searching Authority, Notification of Transmittal of the International Search Report and the Written Opinion of the International Searching Authority, or the Declaration, dated Oct. 18, 2017, pp. 12.

*Primary Examiner* — Matthew D Krcha
(74) *Attorney, Agent, or Firm* — Ference & Associates LLC (57) ABSTRACT

An embodiment provides an apparatus, including: a cartridge including a base and a lid; at least one fluid line located between the base and the lid of the cartridge; at least one heating element located either on the base or the lid and aligned in intimate contact with the at least one fluid line; at least one heat sensing element in intimate contact with the at least one fluid line, where the at least one heat sensing element is spaced downstream from the at least one heating element; a supply of power to the cartridge; and a processor in electrical communication with the cartridge that executes a program of instructions to: operate the at least one heating element to produce heating of the at least one fluid line at a first position; and operate the at least one heat sensing element to detect the heat of a fluid within the at least one fluid line at a position downstream of the first position. Other embodiments are described and claimed.

15 Claims, 6 Drawing Sheets

(51) Int. Cl.
    *G01N 21/78*     (2006.01)
    *G01F 1/684*     (2006.01)
    *G01F 1/688*     (2006.01)
    *G01K 7/22*     (2006.01)
    *G01N 31/22*     (2006.01)
    *G01N 33/18*     (2006.01)

(52) U.S. Cl.
    CPC ............ *G01F 1/6888* (2013.01); *G01N 21/78* (2013.01); *B01L 2200/025* (2013.01); *B01L 2200/147* (2013.01); *B01L 2200/16* (2013.01); *B01L 2300/041* (2013.01); *B01L 2300/046* (2013.01); *B01L 2300/0627* (2013.01); *B01L 2300/0877* (2013.01); *B01L 2300/1827* (2013.01); *B01L 2400/0487* (2013.01); *G01K 7/22* (2013.01); *G01N 31/22* (2013.01); *G01N 33/18* (2013.01)

(56) References Cited

U.S. PATENT DOCUMENTS

| | | | |
|---|---|---|---|
| 6,550,325 | B1 | 4/2003 | Inushima et al. |
| 2008/0210002 | A1 | 9/2008 | Kamiunten et al. |
| 2011/0009817 | A1* | 1/2011 | Bennett .................. A61M 5/168 604/93.01 |
| 2014/0155867 | A1* | 6/2014 | Lee ........................ G01F 1/6847 604/533 |

* cited by examiner

ONLINE CHLORINE ANALYZER

FIELD

The subject matter described herein relates to online water analyzers, specifically online chlorine analyzers.

BACKGROUND

An online chlorine analyzer detects the presence of chlorine in water, e.g., water intended for use in dialysis, other medical applications, or for other uses in which chlorine detection is important. For color based detection, an online chlorine analyzer pumps two reagents from bottles through tubes into a chlorine measurement cell, i.e., a colorimeter. The reagents are mixed with the water sample to be analyzed and time is allowed for a color change of a reagent (e.g., N,N Diethyl-1,4 Phenylenediamine Sulfate, "DPD") in proportion to the amount of chlorine present in the water sample. The DPD reagents, i.e., a buffer and an indicator, are conventionally delivered in an approximate 1:1 ratio before mixing with the sample water and allowing color development to proceed. Color density is a measure of the chlorine concentration and precise optics are employed to measure the color density change using a calibrated light source and a sensitive photodiode integral to the measurement cell.

To make a trustworthy chlorine determination it is imperative to know that reagent delivery has taken place and that the reagents have been delivered simultaneously in the proper ratio. Proper mixing and delivery of a proper volume of sample water is also important but outside the requirements for reagent delivery detection.

BRIEF SUMMARY

One embodiment provides an apparatus, comprising: a cartridge comprising a base and a lid; at least one fluid line located between the base and the lid of the cartridge; at least one heating element located either on the base or the lid and aligned in intimate contact with the at least one fluid line; at least one heat sensing element in intimate contact with the at least one fluid line, wherein the at least one heat sensing element is spaced downstream from the at least one heating element; a means for supplying power to the cartridge; and a processor in electrical communication with the cartridge that executes a program of instructions to: operate the at least one heating element to produce heating of the at least one fluid line at a first position; and operate the at least one heat sensing element to detect the heat of a fluid within the at least one fluid line at a position downstream of the first position.

Another embodiment provides a system, comprising: a housing; a colorimeter disposed within the housing; a cartridge comprising a base and a lid; at least one fluid line located between the base and the lid of the cartridge; at least one heating element located either on the base or the lid and aligned in intimate contact with the at least one fluid line; at least one heat sensing element in intimate contact with the at least one fluid line, wherein the at least one heat sensing element is spaced downstream from the at least one heating element; a means for supplying power to the cartridge; and a processor in electrical communication with the cartridge that executes a program of instructions to: operate the at least one heating element to produce heating of the at least one fluid line at a first position; and operate the at least one heat sensing element to detect the heat of a fluid within the at least one fluid line at a position downstream of the first position.

A further embodiment provides a method of detecting fluid flow in a cartridge comprising: providing a cartridge comprising a base and a lid; providing at least one fluid line having a fluid disposed therein, the at least one fluid line being located between the base and the lid, the fluid line being in fluid communication with a pump; providing at least one heating element located either on the base or the lid and aligned in intimate contact with the at least one fluid line; providing at least one heat sensing element in intimate contact with the at least one fluid line, wherein the at least one heat sensing element is spaced downstream from the at least one heating element; providing a means for supplying power to the cartridge; and providing a processor in electrical communication with the cartridge that executes a program of instructions to: energize the at least one heating element to produce heating of the at least one fluid line at a first position; energize a fluid pump to pump fluid through the at least one fluid line; monitor the at least one heat sensing element to detect the heat of the fluid within the at least one fluid line at a position downstream of the first position; and detecting a rise of the heat signal from the heat sensing element after heat is applied at the first position.

Another embodiment provides a system for chlorine detection in aqueous fluid, comprising: a housing; a colorimeter cell disposed within the housing, the colorimeter cell comprising measurement optics disposed in at least one wall thereof and a lid, wherein at least one wall of the colorimeter cell comprises a weir having a contoured edge; a cartridge disposed proximate to the colorimeter cell; and at least first and second independent fluid lines that enter the housing, traverse through the cartridge and the lid, and have ends thereof exiting a bottom side of the lid; said ends of the at least first and second independent fluid lines being aligned substantially parallel to one another; and said ends of the at least first and second independent fluid lines each positioned to deliver liquid reagents into the colorimeter cell.

In an embodiment, the measurement optics may include a collimating lens and a detector lens; the liquid reagents comprise an indicator and a buffer; wherein the indicator and the buffer are delivered to the colorimeter cell separately using the at least first and second independent fluid lines.

In an embodiment, the lid comprises a plurality of apertures; said at least first and second independent fluid lines traversing said plurality of apertures in a serpentine fashion.

An embodiment may further comprise a pump; wherein the pump is aligned with the cartridge. The pump may be a peristaltic pump, which may operate to simultaneously pump the same volume of liquid reagent from each of the two independent fluid lines into the reaction vessel.

In an embodiment, the lid of the colorimeter cell comprises at least one inlet for one or more additional fluid lines.

In an embodiment, the lid comprises at least two outlets for the additional fluid line, said two outlets being angled towards lateral walls of the colorimeter cell. The lateral walls of the colorimeter cell comprise the measurement optics.

In an embodiment, wherein the measurement optics comprise a light source and a light detector. The light detector is configured to measure light of a predetermined wavelength. In the system, the predetermined wavelength may be a predetermined wavelength range. In the system, the colorimeter cell may include approximately a 22 mm path length.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

BRIEF DESCRIPTION OF THE SEVERAL VIEWS OF THE DRAWINGS

FIG. 4(A-C) illustrates an example colorimeter lid.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

An embodiment provides an online chlorine analyzer. The DPD reagents are moved from separate bottles simultaneously to a colorimeter. In an embodiment, the DPD reagents are moved through separate lines, e.g., one buffer line, one indicator reagent containing line, by a cam-driven linear peristaltic pump whose (two) tube outputs are then processed through the reagent delivery subsystem to verify proper reagent delivery. The reagent delivery subsystem permits indication as to whether appropriate reagent is provided to the colorimeter, as lack of reagent will negate reliable chlorine detection.

Regardless of pump performance, lack of or an improper ratio of DPD reagents may be caused by the simple fact of one or both of the reagent bottles is empty. The possibility also exists that the tubing from the bottle(s) may be clogged or kinked and flow is occluded between the pump and the bottle(s). It is possible that the measurement chamber reagent channels can be partially or totally occluded. Moreover, there is the possibility that leaks exist somewhere in the reagent flow path from bottles to measurement chamber.

The reagent delivery subsystem therefore specifically detects loss of flow and empty bottle/tube conditions with a high degree of certainty.

In an embodiment, the reagent delivery subsystem comprises a thermal flow sensor. The DPD reagent delivery volume is typically only ~50 uL per measurement cycle. Further, the pump tubing is small, with a ~62 thousandths of an inch lumen diameter in the pump necking down to a ~13 thousandths of an inch lumen diameter in the reagent delivery tubes that enter the colorimeter measurement chamber/cell. A normal twelve second pump cycle delivers both DPD reagents simultaneously in the proper volume for a normal measurement cycle. Flushing or priming system actions involve simple extended pump run time; in these cases flow detection is not required.

Therefore it is sufficient for the reagent delivery subsystem to detect proper flow and not actually enumerate the flow rate. In other words, it may be merely necessary to detect that flow is present in both reagent tubes and that flow occurs at the same time in both tubes, precisely coincident with the pump operation.

The illustrated example embodiments will be best understood by reference to the figures. The following description is intended only by way of example, and simply illustrates certain example embodiments.

Figure 1:
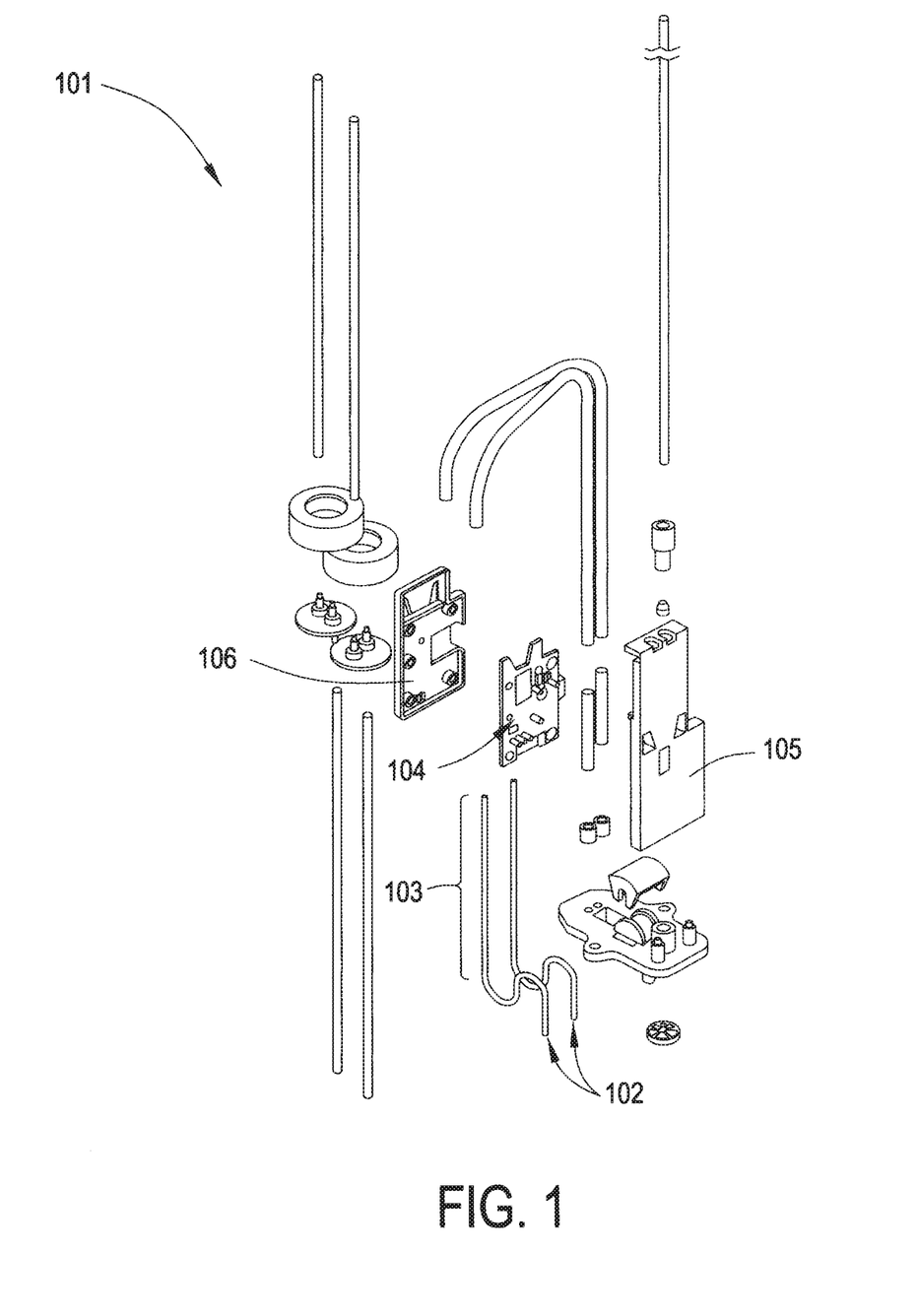
FIG. 1 illustrates an exploded view of a reagent delivery subsystem.

In FIG. 1 an example of a reagent delivery subsystem 101 according to an embodiment is illustrated. As shown, a thermal transfer methodology is used to sense flow in the reagent tubes (collectively indicated at 102). In the thermal approach to flow measurement a portion of the fluid flow path is subjected to a local applied source of external heat or cold, significantly differing from the ambient fluid temperature. If the fluid is flowing, such a thermal 'injection' into the flow can be detected some fixed distance downstream of the injection point. How and for what time duration the thermal injection is applied, and the type of thermal sensor used as a detector, varies by application. With proper timing of measurement, known conditions such as tubing diameter and system calibration, such a system can provide precise flow measurements. The precision of the flow measurement and flow volumes dictate the possible designs that are acceptable for use in a given environment.

The actual flow rate is determined by the pump, and the reagent delivery subsystem 101 needs only to determine that flow in the reagent tubes 102 has actually occurred simultaneously with pump actuation; that is, the actual reagent flow rate need not be determined by the reagent delivery subsystem 101 itself. The reagent delivery subsystem 101 need only detect that flow has occurred in both tubes 102 or if it has not done so, regardless of whether the flow failure is due to no pump action or to empty tubing, etc. Empty tubes can occur for a variety of reasons. Note that complete pump failure can be detected by other system resources, so generally the reagent delivery subsystem 101 detects empty tubes 102 or tubes 102 that are full but demonstrate low or no fluid flow, e.g., due to occlusion somewhere in the flow path.

The reagent delivery subsystem 101 is made to clamp over and around the reagent tubes 102 where they exit the pump, i.e., in the area indicated at 103. The reagent deliver subsystem 101 is non-invasive since the tubing 102 wall is not pierced; it is a flow-through design. Surface mount resistors on a printed circuit board (PCB) 104 are used as a low power heat source and downstream thermistors on PCB 104 are used as thermal sensors, e.g., one for each reagent tube 102. The resistor operation is verified by a third thermistor located proximal to the resistors on PCB 104. As described in further detail in connection with FIG. 2, a fourth thermistor is mounted on the PCB 104, close to the tube sensors (thermistors), to provide a measure of local PCB 104 temperature in the vicinity of the tube sensors.

Mechanically a molded plastic enclosure formed of a cover 105 and base 106, in a clamshell design, contains the PCB 104 and has guides built into it that anchor the tubes 102 while the enclosure is closed around the tubes 102 and fastened close. This permits the reagent delivery subsystem 101 to be modular, i.e., it may be provided as a separate unit that is seated within a larger housing and fitted into place, as further describe herein.

Figure 2:
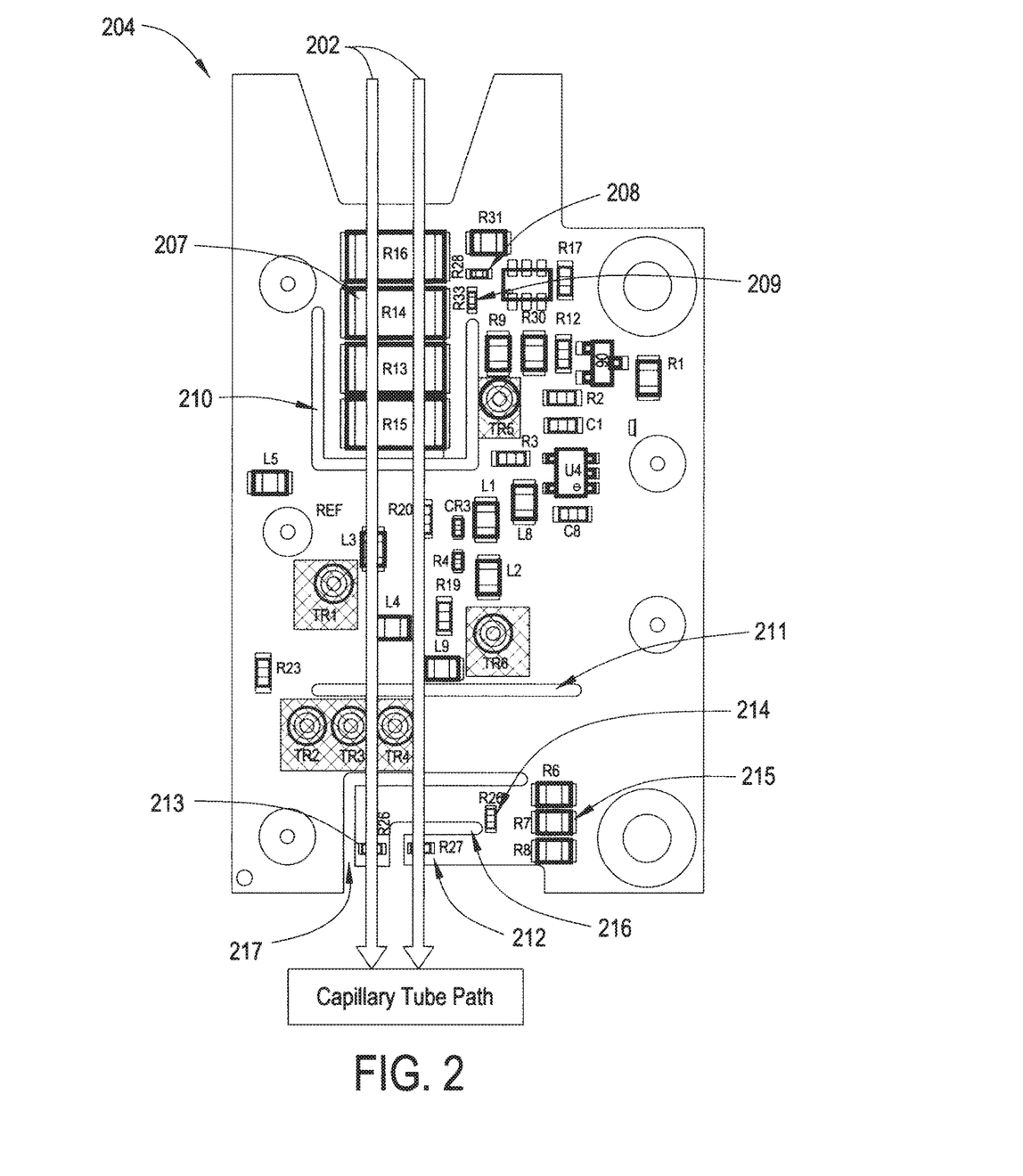
FIG. 2 illustrates a printed circuit board (PCB) of the reagent delivery system of FIG. 1.

Referring to FIG. 2, the tubes 202 are forced into intimate surface contact with the heater resistor(s) 207 and the thermistors 212, 213 to ensure low thermal resistance between the tube 202 external surface and these other elements. A small connector carries only four wires back to the system controller.

In operation, just before a measurement cycle begins, the resistor(s) 207 are turned on for five seconds by the system controller, e.g., via an I2C interface cable. Immediately after the resistor(s) 207 are de-energized, a thirty second pump cycle begins. A four-channel A/D converter scans and delivers all thermistor (212, 213) channel data back to the system controller for flow detection processing.

For safety purposes, the heater thermistor 208 is read before the resistor(s) 207 are energized to determine that the resistor control has not failed and left the resistor(s) 207 on continuously. For redundancy, a dedicated circuit uses a separate heater thermistor 209 to turn off heater power autonomously if an over-temperature condition prevails. With all fully available power applied to the resistor(s) 207 continuously there is no fire hazard or tubing melting or damage. The reagent chemistry may be affected by extreme heating however, potentially causing measurement inaccuracy. A short thermal pulse applied to the tubes 202 for flow detection, however, does not measurably affect the reagent chemistry.

If the tubes 202 are empty or are full but no reagent movement is occurring, the thermistors 212, 213 of PCB 204 will not detect a significant temperature rise in the expected time frame after pumping is initiated, based on the (thermal) time-of-flight principle. This is the salient feature of the reagent delivery subsystem 201 that allows for several forms of analysis to succeed, for loose thermistor tolerances, and for relative temperature measurements to be useful. The tubing sensor 212, 213 digital data may be exported to the system controller for a twelve second window after pumping begins. If there is no fluid flow during this period, the heat pulse simply isn't propagated down the reagent tubes 202 within the time window. Interestingly, a full tube 202 with no flow shows practically no temperature rise, even well into the pumping phase. Empty tubes 202 do conduct heat along the tube wall enough to register a temperature change in the thermistors 212, 213, but such change is both muted and delayed. The entire system returns to thermal equilibrium with ambient conditions before the next measurement cycle occurs.

Because the reagent delivery subsystem 201 is based on thermal changes, tests were performed to determine if ambient temperature of the reagent itself (installation of a fresh reagent bottle at refrigerator temperature) or the tubes 202 and PCB 204 negatively affect the ability to properly detect flow loss. Such tests were performed in an ambient temperature that was five degrees Kelvin above and below the operating temperature specifications. Also, reagent at ice-bath temperature, barely above freezing, was introduced to the reagent delivery subsystem itself 201 at 25° C. Full detection capability was demonstrated in all test cases.

An embodiment provides a thermal interface between the reagent tubes 202 and the PCB 204 components, e.g., 207, 212 and 213, such that the reagent tubes 202 physically touch the components of the PCB 204.

The PCB 204 may be fabricated using 0.031" thick fiberglass epoxy stock instead of the common 0.062" stock. This may be done to reduce the thermal capacitance of the PCB 204 material allowing it to cool faster and not act as a heat reservoir. High thermal impedance slots 210, 216 may be introduced in the PCB 204 material. For example, the high thermal impedance slot 210 thermally insulates the heater resistor(s) 207 from the rest of the PCB 204. Ideally these resistor(s) 207 would transfer heat only to the two reagent tubes 202 running across the top of the resistor(s) 207.

The four resistor(s) 207 illustrated in the example of FIG. 2 are each 49.9 ohm 2512 package resistors arranged in a series-parallel structure, so the total resistance is 49.9 ohms at a nominal power rating of 8 W. These resistor(s) 207 may be driven by an external 15V supply on the controller board, so the drive current is ~300 mA. The tubes 202 are pressed against the top of the resistor(s) 207 using a small silicone foam pad in the enclosure lid 105. This high thermal-resistance pad reduces heat transfer from the tube 202 through the enclosure as well as provides a mechanically compliant pressure to the tube 202. The bottom of the PCB 204 directly under the resistor(s) 207 has small nubs that support the PCB 204 with dimensions trimmed to put a slight pressure load, pressing the reagent tubes 202 between the foam pad and the resistor(s) 207. Farther down the PCB 204 a horizontal high thermal impedance slot 216 in the board helps to thermally insulate the lower thermistor area (sensors 212, 213) from the rest of the PCB 204 area, again acting as thermal resistance from heat conducted across the PCB 204 from the resistor(s) 207. The two tube thermistors 212, 213 are located on slight elongated 'fingers' nearly surrounded by slots (one shown at 216, another at 217) providing thermal resistance from each other and from the rest of the PCB 204 area. The tubes 202 are pressed between the thermistors 212, 213 and the lid of the enclosure (105 of FIG. 1), which provides molded guides for the tubes that allow fast assembly and clamping of the enclosure. The vertical dimensions are adjusted so that the fingers are preloaded with a slight downward pressure and the ends of the fingers are supported below the PCB 204 by raised nubs molded into the enclosure bottom. This ensures a durable thermal interface between the tube 202 wall and the sensor thermistor 212, 213 over time.

Resistors 215 are zero ohm 0603 SMD resistors that are used for the value of the high thermal impedance ceramic substrate in breaking up the copper trace thermal path. It has been found that the copper traces are excellent heat conductors with a thermal resistance far below the PCB 204 material itself. For this reason the smallest feasible trace width of 0.005" is used for connection to components that are thermally sensitive.

The PCB 204 layout uses a copper path trace that surrounds the thermistor sensor 212, 213 area to redirect and diffuse the conducted heat pulse across the PCB 204 away from this area. A similar copper guard ring surrounds the resistor(s) 207 area for similar reasons, but conducts this heat to discrete heat dissipation wings on the top end of the PCB 204.

Between measurement cycles heat is transferred from the PCB 204 to ambient by conduction and natural convection. This cooling phase returns the thermistor sensors 212, 213 to quasi-steady state temperature before the next measurement cycle.

Figure 3:
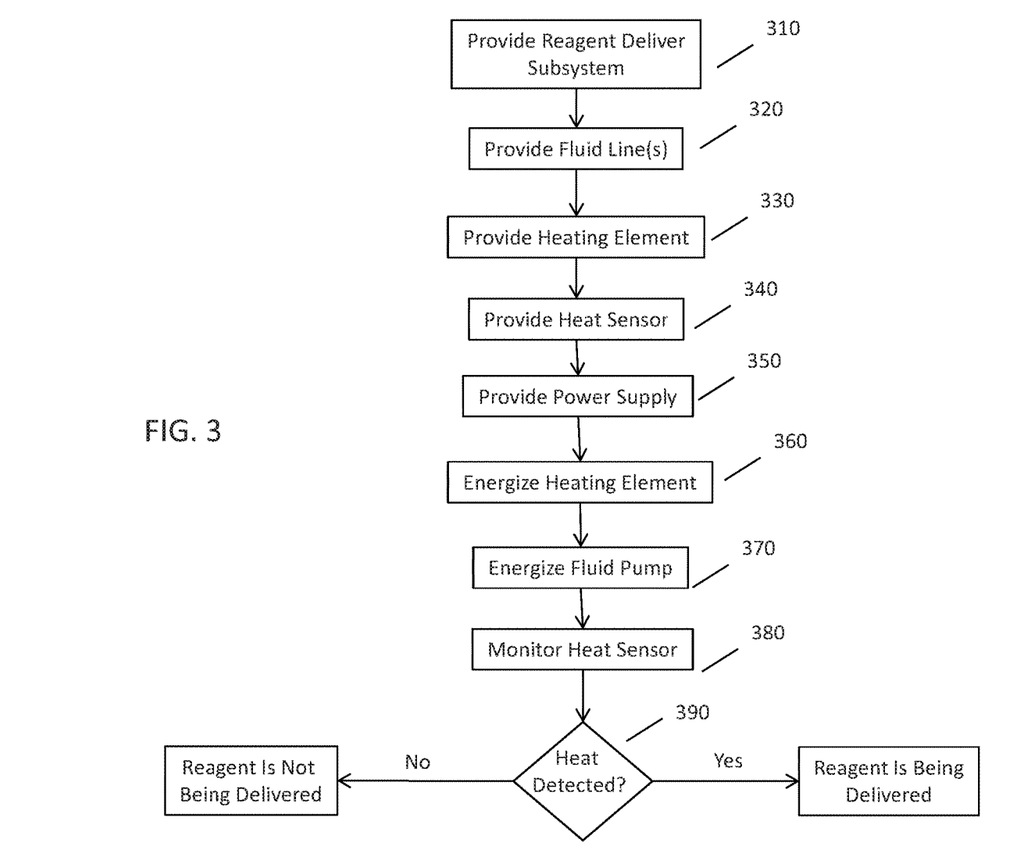
FIG. 3 illustrates an example method of detecting reagent delivery in an online chlorine analyzer.

FIG. 3 illustrates an example method of reagent delivery detection. As described herein, the reagent delivery subsystem may be provided 310 as a cartridge or module that can be mounted into place and connected to existing tubing, e.g., for DPD reagents and a water source. The cartridge may comprise a PCB 104, a base 106 and a lid 106, as well as tubing 102, for example as illustrated for example in FIG. 1.

Indicated at 320, at least one fluid line is provided having a fluid disposed therein, e.g., DPD reagents in tubing 102, where the at least one fluid line is located between the base 106 and the lid 105, the fluid line being in fluid communication with a pump that moves the fluid, as described herein. At least one heating element is provided 330, where the at least one heating element, e.g., resistor(s) 207 is/are located on a component of the base 106 and/or the lid 106 and aligned in intimate contact with the at least one fluid line 102. Also, indicated at 340, at least one heat sensing element, e.g., thermistor(s) 212, 213 is/are provided in intimate contact with the at least one fluid line 102, where the at least one heat sensing element is spaced downstream from the at least one heating element, as for example illustrated in FIG. 2, with the flow direction indicated by the capillary tube path.

A means for supplying power to the cartridge is provided, indicated at 350, as is a processor in electrical communication with the cartridge that executes a program of instructions to perform a reagent delivery detection mechanism, as for example outlined in the following steps.

The at least one heating element is energized at 360 to produce heating of the at least one fluid line at a first position. At 370, the fluid pump is energized to pump fluid through the at least one fluid line, e.g., in the direction of capillary flow and towards the colorimeter.

The at least one heat sensing element is monitored at 380 to detect the heat of the fluid within the at least one fluid line at a position downstream of the first position. Thereafter, at 390 a rise of the heat signal from the thermistor is detected after heat is applied at the first position. This rise of the heat signal detected at 390, or lack thereof, permits the reagent deliver subsystem to detect that the DPD reagents have been moved through the tubing to the colorimeter for trustworthy chlorine detection in the sample water.

The DPD reagents are delivered to a colorimeter cell, where optics disposed in the cell walls detect color change associated with the presence of chlorine. When operating a colorimetric cell that is fed sample water from a pressurized source, there may be entrained or dissolved gases that then nucleate around sites on the surface of the cell in the optical path and form bubbles. The bubbles then interfere with the colorimetric measurement and can cause errors (e.g., up to 100 times) in the measured amount, e.g., as the bubbles grow and move around between the reference and sample measurement.

Figure 4A:
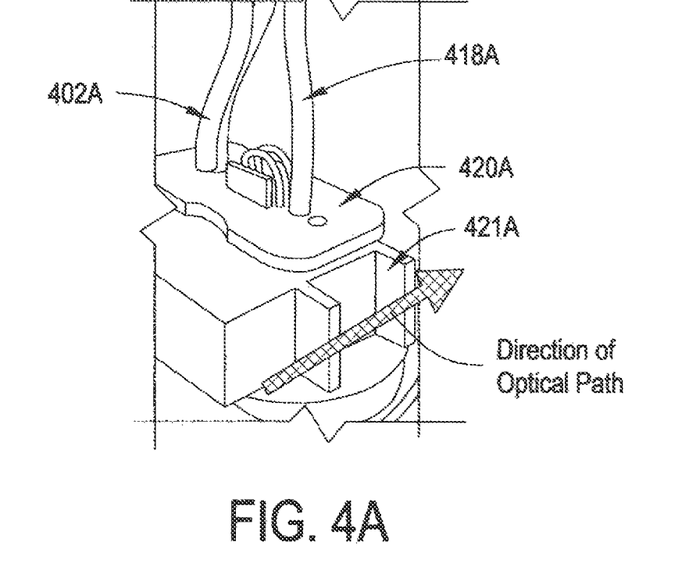
Figure 4B:
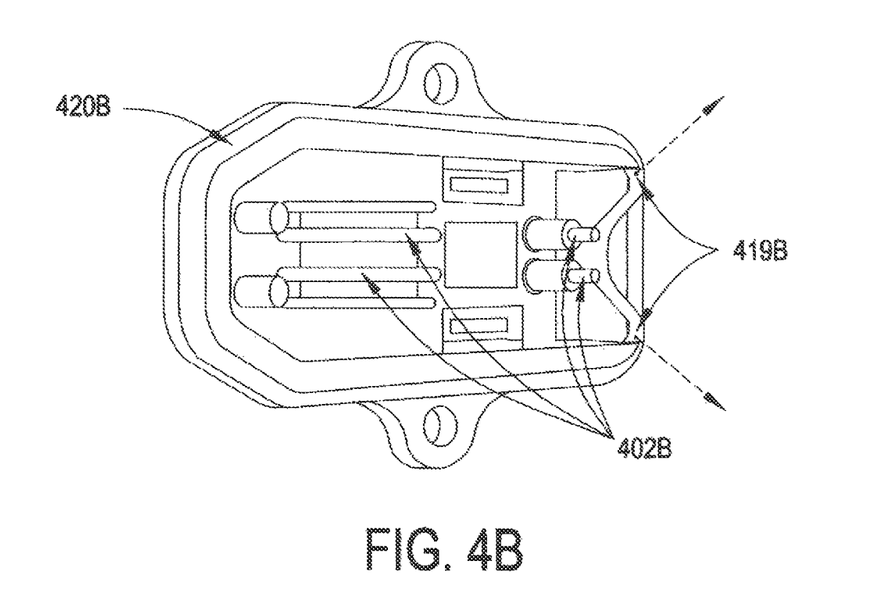

In an embodiment, as illustrated in FIG. 4(A-C), a lid 420A of a colorimetric cell 421A is provided with a plurality of nozzles 419B that direct fluid, e.g., the sample water entering from sample water line 418A into the colorimetric cell 421A at the walls of the cell, over the optics (light source and light detector) and in the optical path running between the light source and the light detector of the colorimetric cell 421A. This permits the sample water to enter from the line 418A, 418B and be directed at the walls of the cell 421A (in the direction indicated by dashed arrows in FIG. 4B) and blow or move away the bubbles before they have a chance to interfere with the optical measurement. DPD reagent lines collectively indicated at 402A in FIG. 4A and 402B in FIG. 4B provide the colorimetric cell with indicator and reagent for colorimetric chlorine detection.

Figure 4C:
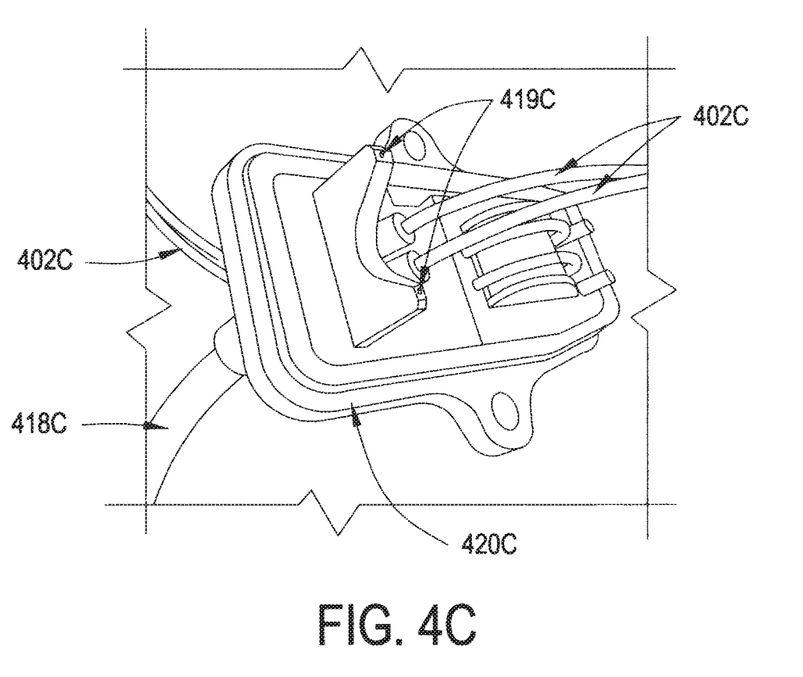

FIG. 4C illustrates another view of the underside of the lid 420C. The nozzles 419C are illustrated as providing outlets for the water line 418C inlet. The DPD reagent lines 402C may or may not be similarly directed toward the walls of the cell 421A.

Figure 5:
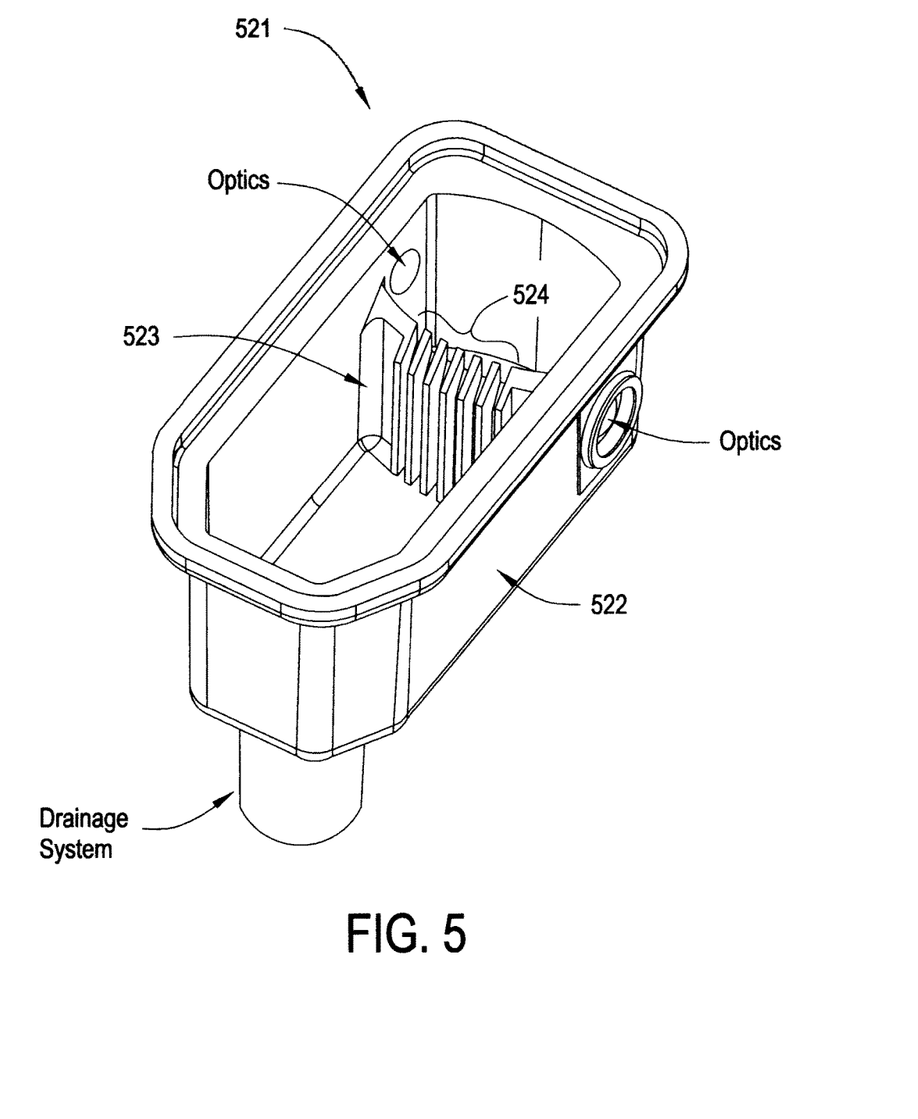
FIG. 5 illustrates an example colorimeter cell.

As shown in FIG. 5, the colorimetric cell 521 includes a main part 522 that forms a reaction cell for sample water, indicator and buffer to react and produce a colored product dependent on the presence of chlorine in the sample water. The color of the sample water is detected using measurement optics of the colorimetric cell 521, e.g., disposed in a wall (which may be of clear or transparent material) of the colorimetric cell 521, specifically a light source and a light detector are utilized to measure color density of the sample water. The measurement optics may include a collimator and/or other conventional optics. The color density of the sample water increases due to the presence of the color created when chlorine oxidizes the DPD or other indicator.

As described herein, a pump is used to provide the DPD reagents and the sample water to the colorimetric cell 521. As the colorimetric cell 521 has a finite volume, the sample water and other liquid (i.e., the buffer and indicator of the DPD reagents) need to exit the colorimetric cell 521.

Accordingly, an embodiment provides a weir 523 in a wall 522 of the colorimetric cell 521. The weir 523 may have a contoured surface 524, as shown, in order to facilitate the smooth outflow of the liquid contents of the colorimetric cell 521. Thus, as the fluid level reaches the top of the weir 523, the fluid flows over the top of the weir 523 and down to a drainage system below. This arrangement permits the colorimetric cell 521 to be flushed with fluid (e.g., sample water) between measurement periods, and also facilitates a consistent fill level within the colorimetric cell 521, allowing for precise volumetric based measurements. The contoured surface 524 of the weir 523 reduces the formation of a large meniscus at the top of the fluid and permits a constant fill volume to be achieved.

It will be readily apparent to those having ordinary skill in the art that various processes described herein may be accomplished via a processor executing a program of instructions, where the program of instructions may be stored in a local memory or accessed remotely. For example, the colorimetric measurements obtained from the cell of the colorimeter may be processed according to a predetermined routine in order to detect the presence of chlorine within the sample water. Similarly, a processor may execute code or instructions to energize various elements, e.g., resistors, and monitor heat developed, e.g., at heat sensors, in order to detect reagent delivery or lack thereof.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. An apparatus, comprising:
   a cartridge comprising a base and a lid;
   at least two fluid lines located between the base and the lid of the cartridge;
   at least one heating element integral to either the base or the lid and aligned in intimate contact with the at least two fluid lines;
   at least one heat sensing element in intimate contact with the at least two fluid lines, wherein the at least one heat sensing element is spaced downstream from the at least one heating element;
   a power supply for the cartridge; and
   a processor in electrical communication with the cartridge programmed to:
      operate the at least one heating element to produce heating of the at least two fluid lines for a predetermined amount of time of at least five seconds at a first position prior to initiation of a measurement cycle, wherein the measurement cycle includes:
         introduction of fluid into the at least two fluid lines upstream from the first position; and
         operation of the at least one heat sensing element to detect the heat of the fluid within the at least two fluid lines at a position downstream of the first position;
      operate the at least one heating element to discontinue heating of the at least two fluid lines at the first position after the predetermined amount of time has passed;
      introduce the fluid into the at least two fluid lines upstream from the first position; and
      operate the at least one heat sensing element to detect the heat of the fluid within the at least two fluid lines at a position downstream of the first position.

2. The apparatus of claim 1, wherein the processor executes the program of instructions to:
   detect a predetermined heating pattern of using the at least one heat sensing element; and
   detect fluid is flowing in the at least two fluid lines from the predetermined heating pattern.

3. The apparatus of claim 1, wherein the at least one heating element comprises at least one resistive heating element.

4. The apparatus of claim 3, wherein the base comprises a printed circuit board, and further wherein the at least one resistive heating elements are disposed on the printed circuit board.

5. The apparatus of claim 1, wherein the at least one heat sensing element comprises a thermistor.

6. The apparatus of claim 5, wherein the base comprises a printed circuit board, and further wherein the thermistor is disposed on the printed circuit board.

7. The apparatus of claim 5 wherein the thermistor comprises a non-linear thermistor.

8. The apparatus of claim 1, wherein the at least two fluid lines comprises two reagent carrying fluid lines.

9. A system, comprising:
   a housing;
   a colorimeter disposed within the housing;
   a cartridge comprising a base and a lid;
   at least two fluid lines located between the base and the lid of the cartridge;
   at least one heating element integral to either the base or the lid and aligned in intimate contact with the at least two fluid lines;
   at least one heat sensing element in intimate contact with the at least two fluid lines, wherein the at least one heat sensing element is spaced downstream from the at least one heating element;
   a power supply for the cartridge; and
   a processor in electrical communication with the cartridge programmed to:
      operate the at least one heating element to produce heating of the at least two fluid lines for a predetermined amount of time of at least five seconds at a first position prior to initiation of a measurement cycle, wherein the measurement cycle includes;
         introduction of fluid into the at least two fluid lines upstream from the first position; and
         operation of the at least one heat sensing element to detect the heat of the fluid within the at least two fluid lines at a position downstream of the first position;
      operate the at least one heating element to discontinue heating of the at least two fluid lines at the first position after the predetermined amount of time has passed;
      introduce fluid into the at least two fluid lines upstream from the first position; and
      operate the at least one heat sensing element to detect the heat of the fluid within the at least two fluid lines at a position downstream of the first position.

10. The system of claim 9, wherein the processor executes the program of instructions to:
    detect a predetermined heating pattern of using the at least one heat sensing element; and
    detect fluid is flowing in the at least two fluid lines from the predetermined heating pattern.

11. The system of claim 9, wherein the at least one heating element comprises a plurality of resistive heating elements.

12. The system of claim 11, wherein the base comprises a printed circuit board, and further wherein the plurality of resistive heating elements are disposed on the printed circuit board.

13. The system of claim 9, wherein the at least one heat sensing element comprises a thermistor.

14. The system of claim 13, wherein the base comprises a printed circuit board, and further wherein the thermistor is disposed on the printed circuit board.

15. The system of claim 9, wherein the at least two fluid lines comprises two reagent carrying fluid lines.

* * * * *